(12) United States Patent
Olivas et al.

(10) Patent No.: US 11,617,837 B2
(45) Date of Patent: Apr. 4, 2023

(54) DRUG DELIVERY DEVICE WITH GEAR MODULE AND RELATED METHOD OF ASSEMBLY

(71) Applicant: AMGEN INC., Thousand Oaks, CA (US)

(72) Inventors: Jerome Olivas, Thousand Oaks, CA (US); Guojie Song, Moorpark, CA (US); Sudeshna Dutta Ray, Thousand Oaks, CA (US)

(73) Assignee: AMGEN INC., Thousand Oaks, CA (US)

( * ) Notice: Subject to any disclaimer, the term of this patent is extended or adjusted under 35 U.S.C. 154(b) by 256 days.

(21) Appl. No.: 16/624,706

(22) PCT Filed: Jul. 11, 2018

(86) PCT No.: PCT/US2018/041569
§ 371 (c)(1),
(2) Date: Dec. 19, 2019

(87) PCT Pub. No.: WO2019/022951
PCT Pub. Date: Jan. 31, 2019

(65) Prior Publication Data
US 2021/0154410 A1 May 27, 2021

Related U.S. Application Data

(60) Provisional application No. 62/536,911, filed on Jul. 25, 2017.

(51) Int. Cl.
*A61M 5/315* (2006.01)
*A61M 5/24* (2006.01)
*A61M 5/145* (2006.01)

(52) U.S. Cl.
CPC .......... *A61M 5/31511* (2013.01); *A61M 5/24* (2013.01); *A61M 5/31575* (2013.01);
(Continued)

(58) Field of Classification Search
CPC ............ A61M 5/1456; A61M 5/14248; A61M 2005/14506; A61M 5/31511; A61M 2005/3152
See application file for complete search history.

(56) References Cited

U.S. PATENT DOCUMENTS

| 3,886,938 A | 6/1975 | Szabo et al. |
| 8,057,434 B2 | 11/2011 | Burroughs et al. |

(Continued)

FOREIGN PATENT DOCUMENTS

| JP | 2007531591 A | 11/2007 |
| JP | 2012521819 A | 9/2012 |

(Continued)

OTHER PUBLICATIONS

International Search Report for International Patent Application No. PCT/US2018/041569, dated Oct. 12, 2018.

(Continued)

*Primary Examiner* — Bradley J Osinski
(74) *Attorney, Agent, or Firm* — Marshall, Gerstein & Borun LLP (57) ABSTRACT

Drug delivery devices and related methods of assembly are disclosed. The drug delivery device may include a main housing having an interior surface defining an enclosed space, and an exterior surface releasably attachable to a patient. A container may be disposed in the enclosed space and include a reservoir containing a drug and a stopper. A drive assembly may also be disposed in the enclosed space and configured to move the stopper through the reservoir to expel the drug from the reservoir. The drive assembly may (Continued)

include a rotational power source and a gear module. The gear module may include a mounting plate and a plurality of gears rotatably connected to the mounting plate. Furthermore, the mounting plate may be separate from the main housing.

12 Claims, 2 Drawing Sheets

(52) U.S. Cl.
CPC ............ *A61M 2005/14506* (2013.01); *A61M 2005/3152* (2013.01)

(56) References Cited

U.S. PATENT DOCUMENTS

| | | | |
|---|---|---|---|
| 8,348,898 B2* | 1/2013 | Cabiri | A61M 5/3204 604/137 |
| 8,430,849 B2 | 4/2013 | Smith et al. | |
| 11,097,055 B2 | 8/2021 | Gibson | |
| 2011/0160666 A1* | 6/2011 | Hanson | A61M 5/1452 702/183 |
| 2018/0085517 A1* | 3/2018 | Laurence | A61M 5/158 |
| 2018/0207358 A1 | 7/2018 | Uchiyama et al. | |
| 2018/0339110 A1* | 11/2018 | Stiffler | A61M 5/24 |

FOREIGN PATENT DOCUMENTS

| | | |
|---|---|---|
| JP | 2013537844 A | 10/2013 |
| JP | 2016539756 A | 12/2016 |
| WO | WO-9607397 A2 | 3/1996 |
| WO | WO-2010/112377 A1 | 10/2010 |
| WO | WO-2014036239 A2 | 3/2014 |
| WO | WO-2015172962 A1 | 11/2015 |
| WO | WO-2016145094 A2 | 9/2016 |
| WO | WO-2017/051619 A1 | 3/2017 |

OTHER PUBLICATIONS

Written Opinion for International Patent Application No. PCT/US2018/041569, dated Oct. 12, 2018.
European Patent Application No. 18746515.8, Communication Pursuant to Article 94(3) EPC, dated Mar. 22, 2021.
Japanese Patent Application No. 2019-571326, Notice of Rejection, dated Apr. 19, 2022.

* cited by examiner

DRUG DELIVERY DEVICE WITH GEAR MODULE AND RELATED METHOD OF ASSEMBLY

CROSS-REFERENCE TO RELATED APPLICATION

This is the United States National Phase of PCT/US2018/041569, filed Jul. 11, 2018, which claims the priority benefit of U.S. Provisional Patent Application No. 62/536,911, filed Jul. 25, 2017, the entire contents of each of which are hereby incorporated herein by reference.

FIELD OF DISCLOSURE

The present disclosure generally concerns drug delivery devices and, more particularly, the configuration and manufacture of a drive assembly for expelling a drug from a reservoir included in a drug delivery device.

BACKGROUND

Drug delivery devices, such as injectors, are used to deliver liquid drugs to a patient. Many drug delivery devices are configured to expel a drug stored within an internal reservoir through a needle, cannula, or other delivery member into the patient. Certain drug delivery devices include a drive assembly to provide the actuation energy necessary for discharging the drug from the reservoir. Some drive assemblies include a rotational power source such as an electric motor. In certain cases the torque and/or rotational speed that is output by the rotational power source may need adjusting prior to its transmission to the element responsible for discharging the drug from the reservoir. For instance, it may be necessary to lower the rotational speed output by an electric motor while increasing torque in order to achieve a desired rate of drug delivery.

Certain drug delivery devices incorporate a plurality a gears to provide speed and/or torque conversions from the rotational power source to the discharging element. Conventional designs mount such gears directly to the wall of the main housing of the drug delivery device. Handling of the drug delivery device, by the patient or during manufacturing or shipping, as well as other external forces, may cause the wall of the main housing to deform, particularly since the wall is usually made of a stiff but lightweight and semi-flexible material such as plastic. The gears of a conventional drug delivery device are attached directly to the wall of the main housing, and thus warping and other changes to the shape of the wall of the main housing can result in misalignment of the gears. This problem is exacerbated by gears having small teeth and/or that require precise alignment, which oftentimes is the case in a drug delivery device.

Furthermore, mounting the gears directly to the wall of the main housing can make it difficult to inspect the gears after they have been installed in the drug delivery device. This is because other components within the main housing may obstruct the gears from view after they are mounted. The diminished ability to inspect the gears may allow some manufacturing flaws, such as misalignment of the gears, to go unnoticed. This in turn increases the risk that the drug delivery device will operate improperly when activated by a patient, and potentially deliver an incorrect dose of the drug.

The present disclosure sets forth drug delivery devices and related methods of assembly embodying advantageous alternatives to existing drug delivery devices and methods of assembly, and that may address one or more of the challenges or needs mentioned herein, as well as provide other benefits and advantages.

SUMMARY

One aspect of the present disclosure provides a drug delivery device including a main housing, a container, and a drive assembly. The main housing may include an interior surface defining an enclosed space, and an exterior surface releasably attachable to a patient. The container may be disposed in the enclosed space and include a reservoir containing a drug and a stopper. The drive assembly may be disposed in the enclosed space and configured to move the stopper through the reservoir to expel the drug from the reservoir. The drive assembly may include a rotational power source and a gear module. The gear may include a mounting plate and a plurality of gears rotatably connected to the mounting plate. The mounting plate may be separate from the main housing.

Another aspect of the present disclosure provides a method of assembly, including: (a) connecting a plurality of gears to a mounting plate of a gear module; (b) installing the gear module in a main housing of the drug delivery device after connecting the plurality of gears to the mounting plate; and (c) enclosing the gear module and a container having a reservoir containing a drug within the main housing of the drug delivery device.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the exemplary embodiments, except as may be explicitly delineated in the corresponding written description. Also, none of the drawings is necessarily to scale.

DETAILED DESCRIPTION

In general terms, the present disclosure is concerned with the configuration and manufacture of an internal drive assembly of a drug delivery device. The drive assembly may be configured to provide the actuation energy necessary for discharging a drug from a reservoir included in the drug delivery device. More particularly, the drive assembly may force a stopper through the reservoir in a controlled manner to expel the drug to a patient upon activation of the drug delivery device. According to the present disclosure, the drive assembly may include a gear module which is constructed and/or installed independently of other elements of the drug delivery device. The gear module may include a plurality of gears which receive rotational power from a rotational power source, and a mounting plate to which the gears are rotatably connected. The mounting plate may provide a rigid support structure for the gears and may be constructed as a separate component from a main housing of the drug delivery device. As such, the mounting plate may shield the gears from any unintentional, or intentional, warping or bending of a wall defining the main housing. Accordingly, the mounting plate advantageously reduces the likelihood of misalignment of the gears subsequent to their installation in the drug delivery device. Furthermore, use of the mounting plate permits more flexibility in the design and/or materials used to construct the main housing, and may do so without compromising the integrity of the drug delivery device. Additionally, the presently disclosed gear module can be pre-assembled and inspected for flaws prior to its installation in the drug delivery device. This may reduce the need for an extensive inspection of the gears after their installation in the main housing, where they may be partially or entirely obstructed from view.

Each of the foregoing components of the drug delivery device and methods of assembling such a device will now be described in more detail.

Figure 1:
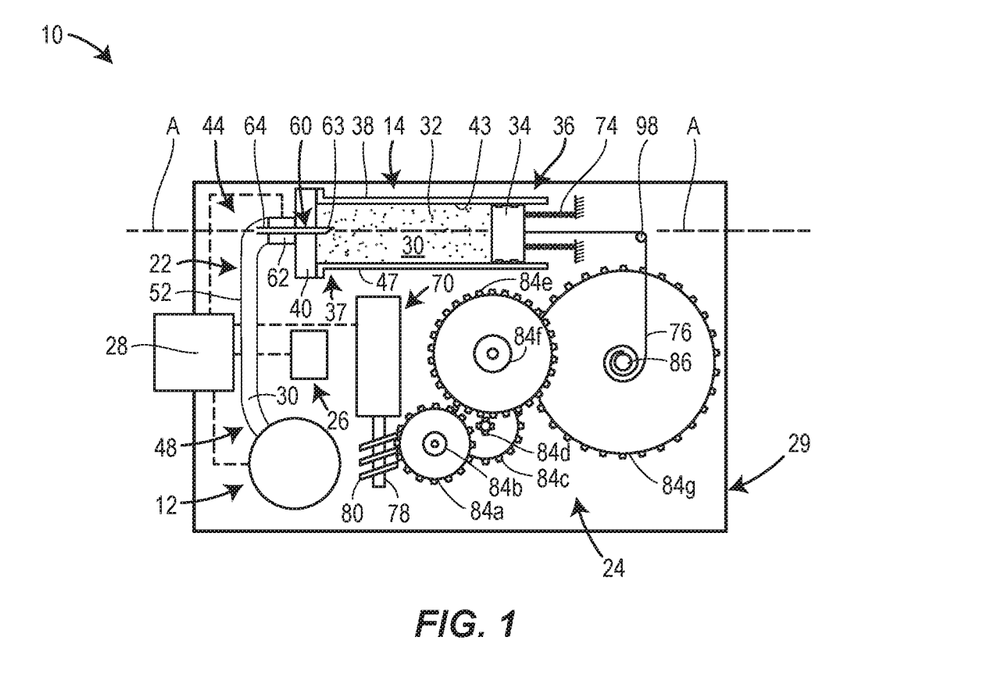
FIG. 1 is schematic top view of an embodiment of a drug delivery device in accordance with principles of the present disclosure.
Figure 2:
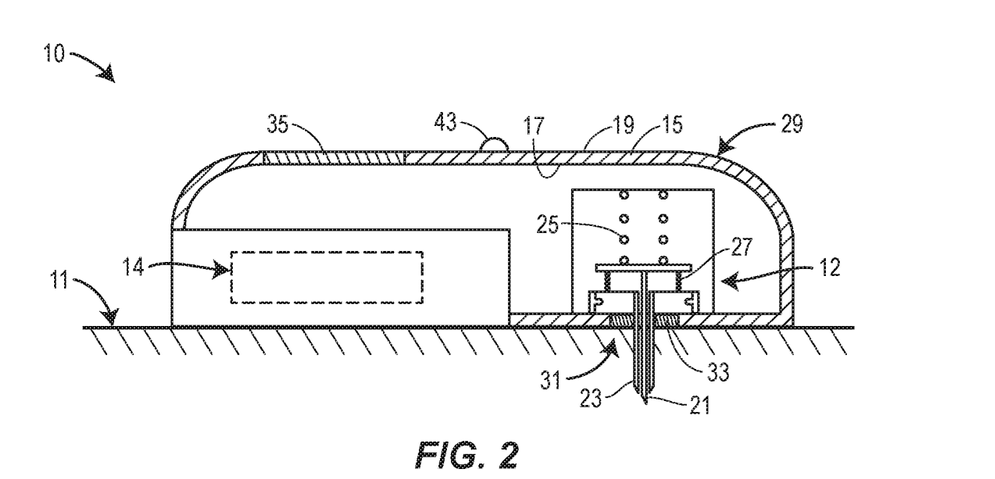
FIG. 2 is a schematic partial cross-sectional side view of the drug delivery device shown in FIG. 1.

FIGS. 1 and 2 are schematic illustrations of one embodiment of a drug delivery device 10 constructed in accordance with the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, which is releasably attached to the patient's tissue 11 (e.g., the patient's skin). In other embodiments (not illustrated), the drug delivery device 10 may be configured as a pen-type injector, such as an autoinjector or injection pen, which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container 14, a fluid pathway assembly 22, a drive assembly 24, and a controller 26, each of which may be disposed within an interior enclosed space of a main housing 29. An input device 28 (e.g., a user-depressible button, touchscreen, microphone, etc.) may protrude through or otherwise be disposed at an exterior surface 19 of the main housing 29 and may be configured to initiate operation of the drug delivery device 10 by activating, via mechanical and/or electrical means (shown in dotted lines in FIG. 1), the insertion mechanism 12, the fluid pathway assembly 22, the drive assembly 24, the controller 26, and/or other mechanisms and/or electronics. In embodiments where the input device 28 is a button that is depressed or otherwise physically moved by a user or patient, the input device 28 may operate as an actuator that exerts the a motive force needed to activate the insertion mechanism 12, the fluid pathway assembly 22, the drive assembly 24, the controller 26, and/or other mechanisms. In such embodiments, the input device 28 may be physically connected to, either directly or indirectly via a mechanical linkage, the insertion mechanism 12, the drive assembly 24, the fluid pathway assembly 22, and/or other mechanisms, such that manually depressing or otherwise interacting with the input device 28 supplies the motive force necessary to activate the insertion mechanism 12, the drive mechanism 24, the fluid pathway assembly 22, and/or other mechanisms. For example, in some embodiments, manually depressing the input device 28 may cause the fluid pathway assembly 22 to move towards the stationary container 14, or alternatively cause the container 14 to move towards the stationary fluid pathway assembly 22, and thereby cause a container access needle to penetrate through a seal member into a reservoir or interior volume of the container 14. Additionally or alternatively, depressing or otherwise interacting with the input device 28 may transmit an electrical and/or mechanical signal to the controller 26, which in turn may execute programmable instructions to control operation of the insertion mechanism 12, the drive assembly 24, and/or the fluid pathway assembly 22. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the input device 28 and which, in response to an electrical control signal received from the controller 26, exerts the motive force needed to activate the insertion mechanism 12, the drive assembly 24, the fluid pathway assembly 22, and/or other mechanisms. One example of such an internal actuator is the rotational power source of the drive assembly 24, which is described in more detail below.

Referring to FIG. 2, the main housing 29 may include a wall 15 having an interior surface 17 and an exterior surface 19. The wall 15 may be a single unitary structure or made of multiple distinct structures interconnected with each other. The interior surface 17 of the wall 15 may define an enclosed space in which the insertion mechanism 12, the container 14, the fluid pathway assembly 22, the drive assembly 24, and the controller 26, and/or other mechanisms and/or components may be disposed. In some embodiments, the enclosed spaced may be sealed shut to define an enclosed clean space having, for example, a sterile or aseptic internal atmosphere. The exterior surface 19 of a bottom portion of the wall 15 may be releasably attachable to the patient's tissue 11. In some embodiments, this may be accomplished with a skin adhesive applied to or otherwise disposed at the exterior surface 19 of the bottom portion of the wall 15 of the main housing 29. In some embodiments, the skin adhesive may be part of an adhesive patch attached to the exterior surface 19 of the bottom portion of the wall 15 of the main housing 29. The exterior surface 19 of a top portion of the wall 15 may include one or more visual indicators 42 (e.g., lights, graphical displays, etc.) and/or a window 35 for viewing the container 14 and the drug 32 contained therein. The one or more visual indicators 42 may be used to communicate information to the user about the operational state of the drug delivery device 10 and/or the condition of the drug 32. An opening 31 may be formed in the bottom portion of the wall 15, and optionally a pierceable sterile barrier 33, such as a pierceable septum, may extend across the opening 31 to seal the interior of the main housing 29 prior to use. In some embodiments, the pierceable sterile barrier 33 may be omitted, and instead a removable sealing member (not illustrated) may cover and seal close the opening 31 prior to use.

More particularly with respect to the window 35, this element may be constructed of a transparent or semi-transparent material and generally aligned with the container 14, so as to allow a patient or user of the drug delivery device 10 to inspect the drug 32 within the container 14 and/or confirm dose completion. Suitable materials for constructing the window 35 include, but are not limited to, glass and/or plastic. The location of the window 35 on the exterior of the drug delivery device 10 may expose the drug 32 to ambient light including sunlight. Some drugs may be sensitive to certain wavelengths of light and undergo undesirable molecular changes when exposed to such wavelengths of light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the main housing 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 14, while filtering out up to and including approximately (e.g., ±10%) 50% of light in the visible range. In some embodiments, the portion of visible light filtered out by the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the eye strength of the patient population of the drug 32, among other considerations. Adding the polarized filter to the window 35, in lieu adding a dark tint to the window 35 and/or shrinking the size of the window 35, advantageously protects the drug 35 from light in the visible range without substantially compromising the ability of the patient or user of the drug delivery device 10 to inspect the drug 32 within the container 14.

After the bottom portion of the wall 15 of the main housing 29 is attached to the patient's tissue 13, the insertion mechanism 12 may be activated to move a subcutaneous delivery member from a retracted position, where a pointed distal end of the subcutaneous delivery member is withdrawn within the main housing, to a deployed position, where the pointed distal end projects from the main housing 29 beyond the exterior surface 19 of the main housing 29. In the present embodiment, this may include the insertion mechanism 12 inserting a trocar 21 and a hollow cannula 23 surrounding the trocar 21 through the pierceable sterile barrier 33 and into the patient's tissue 11, as illustrated in FIG. 2. Immediately or shortly thereafter, the insertion mechanism 12 may automatically retract the trocar 21, leaving the distal end of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. The distal end of the cannula 23 may be sharpened to a point but may be more blunt than the distal end of the trocar 21. In other embodiments (not illustrated), the trocar 21 and cannula 23 may be omitted, and instead the insertion mechanism 12 may insert only a rigid, hollow needle into the patient's tissue 13 for subcutaneous delivery of the drug 32. Also, in one or more of these embodiments, the subcutaneous delivery member may have a longitudinal axis that is perpendicular to or otherwise non-parallel to the longitudinal axis A of the container 14.

Still referring to FIG. 2, the insertion mechanism 12 may include an insertion biasing member 25 and a retraction biasing member 27. Prior to activation of the insertion mechanism 12, each of the insertion biasing member 25 and the retraction biasing member 27 may be retained in an energized state. Upon activation of the insertion mechanism 12 via, e.g., the input device 28, the insertion biasing member 25 may release its stored energy to move the subcutaneous delivery member from the retracted position to the deployed position. In the illustrated embodiment, this involves moving the trocar 21 and the cannula 23 from a position where their distal ends are located within the main housing 29, to the position shown in FIG. 2. The retraction biasing member 27 may be retained in its energized state during the insertion procedure. Subsequent to the insertion procedure, the retraction biasing member 27 may release its stored energy to move the trocar 21 from the deployed position back to the retracted position, leaving the cannula 23 in the deployed position.

In the embodiment illustrated in FIG. 2, the insertion biasing member 25 and the retraction biasing member 27 are respective compression springs which are arranged concentrically with each other. Other power sources for the insertion biasing member 25 and/or the retraction biasing member 27 are also possible, including, for example, a torsion spring, an electric motor, a hydraulic or pneumatic pump, or a canister that releases a pressurized gas or a pressurized liquid to provide actuation energy. In some embodiments, the insertion biasing member 25 and the retraction biasing member 27 may be defined by a single electric motor which is operated in a forwards and a reverse direction to provide the insertion and retraction movements. Also, in some embodiments, the retraction biasing member 27 may be omitted.

Referring back to FIG. 1, the container 14, which in some contexts may be referred to as a primary container, may include a wall 38 with an interior surface 43 defining a reservoir 30 that is filled with the drug 32 and an exterior surface 47. In some embodiments, the reservoir 30 may be pre-filled with the drug 32 by a drug manufacturer prior to installation of the container 14 in the drug delivery device 10. In some embodiments, the container 14 may be rigidly connected to the housing 29 such that the container 14 cannot move relative to the housing; whereas, in other embodiments, the container 14 may be slidably connected to the main housing 29 such that the container 14 can move relative to the main housing 29 during operation of the drug delivery device 10. The container 14 may have an elongate, barrel-like or cylindrical shape extending along a longitudinal axis A. In embodiments where the drug delivery device 10 is configured as an on-body injector, the longitudinal axis A of the container 14 may be perpendicular or substantially perpendicular, or otherwise non-parallel, to a direction in which the insertion mechanism 12 inserts the subcutaneous delivery member such as the cannula 23 into the patient. This configuration may allow the on-body injector to have a generally planar, low-profile shape that can be worn by the patient without impeding the patient's movement. Initially, a stopper 34 or other piston member may be positioned in the reservoir 30 at a proximal end 36 of the container 14. The stopper 34 may sealingly and slidably engage the interior surface 43 of the wall 38 of the container 14, and may be movable relative to the wall 38 of the container 14 to expel the drug 32 container therein.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 30 may be completely or partially filled with the drug 32. The drug 32 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive assembly 24 may push the stopper 34 along the longitudinal axis A through the reservoir 30 from the proximal end 36 of the container 14 to a distal end 37 of the container 14 in order to expel the drug 32. As described below in more detail, the drive assembly 24 may include a rotational power source, a gear module configured to convert the rotational speed and/or torque of the rotational movement output by the rotational power source, a stopper biasing member initially retained in an energized state and configured to axially expand to move the stopper through the reservoir 30, and a tether configured to restrain or otherwise regulate the expansion of the stopper biasing member.

At the distal end 37 of the container 14, an opening 45 may be formed in the wall 38. At least prior to operation of the drug delivery device 10, the opening 45 may be covered and sealed closed by a seal member 40, such as a pierceable septum, connected to the distal end 37 of the container 14. A proximal end surface of the seal member 40 and the interior surface 43 of the wall 38 of the container 14 may define the reservoir 30. Additionally, in some embodiments, a distal end surface of the stopper 34 may define the reservoir 30.

Generally, the seal member 40 may be configured to selectively permit access to the reservoir 30. During operation of the drug delivery device 10, the seal member 40 may be physically altered (e.g., pierced) to permit fluid communication with the drug 32 in the reservoir 30. In some embodiments, the seal member 40 may be constructed of a flexible or elastically deformable material such as rubber, for example, which is capable of being penetrated or pierced by a sharpened end or point 63 of a container access needle 60 of the fluid pathway assembly 22. In some embodiments, the seal member 40 may be clamped or otherwise secured to the distal end surface of the wall 38 of the container 14 by a fastener (e.g., a crimp ring) and/or adhered directly to the distal end surface of the wall 38 of the container 14.

Still referring to FIG. 1, the fluid pathway assembly 22 may be configured to establish fluid communication between the container 14 and the insertion mechanism 12 via a sterile fluid flow path during operation of the drug delivery device 10. Prior to use of the drug delivery device 10, the fluid pathway assembly 22 may not be in fluid communication with the container 14. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 14 and the fluid pathway assembly 22. Subsequently, the drive assembly 24 may move the stopper 34 in the distal direction relative to the wall 38 of the container 14 to force the drug 32 stored in the container 14 through the sterile fluid flow path of the fluid pathway assembly 22 and into the cannula 23 or needle or other delivery member of the insertion mechanism 12 for subcutaneous delivery to the patient.

In some embodiments, the fluid pathway assembly 22 may be rigidly connected to the wall 15 of the main housing 29 such that the fluid pathway assembly 22 cannot move relative to the main housing 29; whereas, in other embodiments, the fluid pathway assembly 22 may be slidably or moveably connected to the wall 15 of the main housing 29 such that the fluid pathway assembly 22 can move relative to the main housing 29 during operation of the drug delivery device 10. In the former embodiments, the container 14 may be slidably or moveably connected to the wall 15 of the main housing 29 such that the seal member 40 can be moved toward and pierced by the point 63 of the stationarily arranged container access needle 60 of the fluid pathway assembly 22. In the latter embodiments, the container 14 may be stationarily positioned relative to the main housing 29 while the fluid pathway assembly 22 is moved toward the container 14, causing the point 63 of the container access needle 60 to pierce through the seal member 40 and access the reservoir 30.

The fluid pathway assembly 22 may include a first end 44 connected to the container 14, a second end 48 connected to the insertion mechanism 12, and a fluid passage 50 extending between the first end 44 and the second end 48. The fluid passage 50 may be sterilized, and may be partially or entirely made of a flexible tubing 52. Initially, there may be slack in the flexible tubing 52 to allow the fluid pathway assembly 22 to move relative to the housing 29 and/or to allow components of the insertion mechanism 12 to which the fluid pathway assembly 22 is attached to move relative to the housing 29. In some embodiments, the fluid passage 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway assembly 22. Furthermore, the fluid restrictor element may be made of a more rigid material than the flexible tubing 52. For example, the fluid restrictor element made be made of metal, whereas the flexible tubing 52 may be made of a polymeric material such as plastic.

Still referring to FIG. 1, the first end 44 of the fluid pathway assembly 22 may include the container access needle 60 and a connection hub or mounting member 62. The container access needle 60 may have a sharpened end or point 63, corresponding to a proximal end of the container access needle 60, and a distal end 64 in fluid communication with the fluid passage 50. The mounting member 62 may cover a length of the distal end 64 of the container access needle 60 and connect the distal end 64 of the container access needle 60 to the flexible tubing 52.

The container access needle 60 may possess a hollow, tubular shape with one or more openings at each of the point 63 and the distal end 64. The container access needle 60 made be constructed of a rigid material including, but not limited to, metal (e.g., stainless steel) and/or plastic. In some embodiments, the mounting member 62 may be constructed of a different material than the container access needle 60 such that the mounting member 62 and the container access needle 60 are separate, but rigidly connected, components. In some embodiments, the mounting member 62 may be constructed of a rigid plastic material whereas the container access needle 60 may be constructed of metal. In other embodiments, the mounting member 62 and the container access needle 60 may be made of the same material such that they form a single, unitary one-piece structure.

Figure 3:
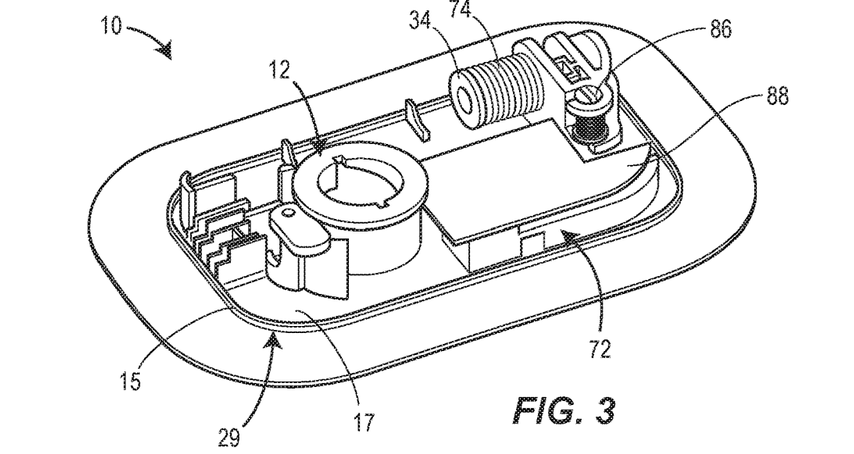
FIG. 3 is a perspective view of the drug delivery device of FIG. 1, with several components omitted including the container, fluid pathway assembly, tether, and top portion of the wall of the main housing.
Figure 4:
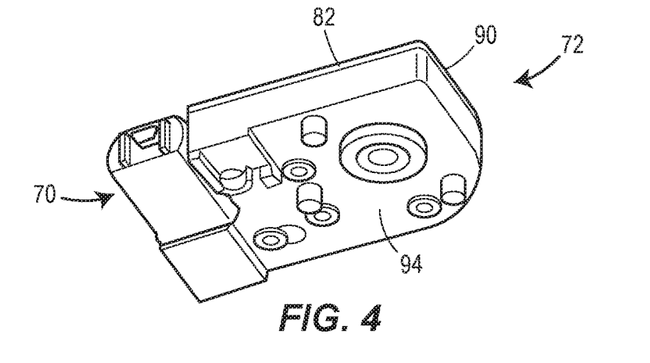
FIG. 4 is a perspective top view of an embodiment of a gear module in accordance with principles of the present disclosure.
Figure 5:
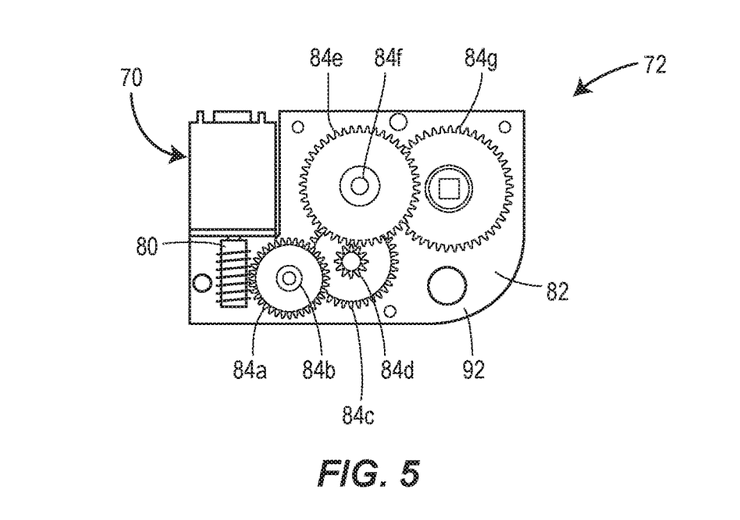
FIG. 5 is a top view of the gear module illustrated in FIG. 5, with the cover member omitted to reveal the gears container within the gear module.

With continued reference to FIG. 1, and additionally FIGS. 3-5, further description of the drive assembly 24 is provided. Generally, the drive assembly 24 may be configured to impart the motive force needed to, at least, move the stopper 34 through the reservoir 30 and thereby expel the drug 32 via the container access needle 60. In some embodiments, the drive assembly 24 may be activated in response to a mechanical and/or electrical signal generated by the user's depression or other interaction with the input device 28; whereas, in other embodiments, the drive assembly 24 may be activated in response to an electrical signal received from the controller 26. Furthermore, in some embodiments, in addition to activating the drive assembly 24, the controller 26 may monitor and/or control the operation of the drive assembly 24 in order to regulate the rate and/or timing with which the stopper 34 expels the drug 32 from the reservoir 30.

The drive assembly 24 may include a rotational power source 70 configured to output rotational movement, a gear module 72 configured to convert the speed and/or torque of the rotational movement output by the rotational power source 70, a stopper biasing member 74 initially retained in an energized state and configured to axially expand to move the stopper 34 through the reservoir 30, and a tether 76 configured to restrain or otherwise regulate the expansion of the stopper biasing member 74.

The rotational power source 70 may be any mechanism capable of converting stored energy into rotational mechanical motion, including, but not limited to, an electric motor, a torsion spring, and/or a hydraulic or pneumatic pump. In the case of an electric motor, the drug delivery device 10 may include a battery for storing electrical energy for use by the rotational power source 70. The rotational power source 70 may possess a rotatable output shaft 78 for transferring rotational motion to the gear module 72. As shown in FIG. 5, a screw or worm gear 80 may be mounted on and axially aligned with the output shaft 78, and include spirally-cut teeth which meshingly engage with teeth of one of the spur gears included in the gear module 72. During operation, the worm gear 80 may rotate relative to the mounting plate 82 of the gear module 72. In some embodiments, the rotational power source 70 may be mounted to the wall 15 of the main housing 29 separately or independently of the gear module 72; whereas, in other embodiments, the rotational power source 70 may be pre-attached directly to the gear module 72 such that mounting the gear module 72 to the wall 15 of the main housing 29 results in mounting the rotational power source 70 within the main housing 29. In such latter embodiments, the rotational power source 70 and the gear module 72, though separate components, may be installed in the main housing 29 as a single unit. Furthermore, in alternative embodiments, a bevel gear may be substituted for the worm gear 80.

In some embodiments, the worm gear 80 may have a self-locking configuration, such that the worm gear 80 can drive the gear 84a but the gear 84a cannot drive (or will have extreme difficulty driving) the worm gear 80. The self-locking configuration may depend on a lead angle, a pressure angle, and/or a coefficient of friction between the worm gear 80 and the gear 84a. The self-locking configuration of the worm gear 80 may, via the tether 76, help prevent premature expansion or creep of the stopper biasing member 74 prior to operation of the rotational power source 70.

Referring to FIGS. 3-5, the gear module 72 generally functions as a gearbox and may include a mounting plate 82 and a plurality of gears 84a-g. Each of the gears 84a-g may be rotatably connected to the mounting plate 82 such that each of the gears 84a-g can rotate relative to the mounting plate 82. In some embodiments, the rotatable connection for any individual one of the gears 84a-g may be achieved by a pin or shaft which is rigidly attached to the gear and slidably received in a groove or recess formed in a top surface 92 the mounting plate 82. In some embodiments, each gear of the gears 84a-g may be a spur gear having a plurality of a teeth either straight or helically cut into an outer circumferential surface of the gear. The teeth of each gear of the plurality of gears 84a-g may meshingly engage with the teeth of at least one other gear of the plurality of gears 84a-g during operation of the rotational power source 70. The gear 84a, which may function as the input gear of the gear module 72, may have teeth which meshingly engage with the teeth of the worm gear 80 such that the gear 84a receives rotational power from the rotational power source 70. The gear 84g, which may function as the output gear of the gear module 72, may be connected to and axially aligned with a winch drum 86 such that the gear 84g outputs rotational movement to the winch drum 86. Due to a gear reduction provided by the gear module 72, the rotational movement output to the winch drum 86 may have a lower rotational speed and, in some cases, a higher torque, than the rotational movement output by the rotational power source 70. The gear reduction may be achieved by configuring at least some of the gears 84a-g with different outer diameters and/or different numbers of teeth.

Certain pairs of the gears 84a-g may be arranged in parallel, that is sharing a common rotational axis; whereas other pairs of the gears 84a-g may be arranged in series, that is having rotational axes that are offset and parallel to each other yet still having teeth that meshingly engage each other. As illustrated in FIG. 5, the following gear pairs may be arranged in parallel: (i) gears 84a and 84b; (ii) gears 84c and 84d; and (iii) gears 84e and 84f. By contrast, the following gear pairs may be arranged in series: (i) gears 84b and 84c; (ii) gears 84d and 84e; and (iii) gears 84f and 84g. In some embodiments, such as the one illustrated in FIG. 5, the number of gear pairs arranged in series may be equal to three, or less than three in other embodiments, in an effort to reduce components and increase reliability. The worm gear 80 and the spur gear 84a are also a gear pair that may be arranged in series.

As seen in FIG. 3, the mounting plate 82 may be connected to, but separate from, the wall 15 of the main housing 29. In some embodiments, the mounting plate 82 may be connected to the wall 15 via a fastener such as a screw or bolt, for example. By virtue of being mounted on the mounting plate 82, the gears 84a-g are not directly connected to the wall 15 of the main housing 29. Accordingly, bending or other deformations to the wall 15 of the main housing 29 are less likely to affect the alignment of the gears 84a-g. In some embodiments, the mounting plate 82 may be constructed of a more rigid material and/or thicker material than the wall 15 of the main housing 29, so as to render the mounting plate 82 less susceptible to bending than the wall 15 of the main housing 29. Furthermore, since the mounting plate 82 provides a rigid support structure for the gears 84a-g, there may be more design freedom with respect to the shape and/or materials used construct the wall 15 of the main housing 29. Additionally, a printed circuit board 88 associated with the controller 26 may be connected directly to the mounting plate 82, instead of to the wall 15, as shown in FIG. 3.

Referring to FIGS. 4 and 5, the mounting plate 82 may include a bottom surface 90 and a top surface 92. The bottom surface 90 may face the interior surface 17 of the wall 15 of the main housing 29 when the gear module 72 is installed in the main housing 29. The gears 84a-g may be rotatably connected to the top surface 92 of the mounting plate 82. The gear module 72 may additionally include a cover member 94 to at least partially enclose the gears 84a-g within the gear module 72. As shown in FIG. 4, the cover member 94 may be positioned above the top surface 92 of the mounting plate 82 such that the gears 84a-g are positioned between the cover member 94 and the top surface 92 of the mounting plate 82.

Referring back to FIGS. 1 and 3, the drive assembly 24 may include one or more components for operationally connecting the gear module 72 to the stopper 34. In some embodiments, these components may include a tether 76, a winch drum 86, and a pulley member 98. The tether 76 may be any flexible elongate member such as a cord, wire, and/or chain, for example. The tether 76 may include a first end connected, directly or indirectly, to the winch drum 86 and a second end connected, directly or indirectly, to the stopper 34 and/or the stopper biasing member 74. Initially, prior to operation of the rotational power source 70, a length of the tether 76 may be wound around the winch drum 86 as shown in FIG. 1. The winch drum 86 may be rigidly mounted on the output gear 84g such that the winch drum 86 rotates jointly together with the output gear 84g about a common rotational axis relative to the main housing 29. A portion of the tether 76 between the winch drum 86 and the stopper 34 may be pulled taught partially around the pulley member 98 in order to change the direction of the tether 76. As shown in FIG. 1, the pulley member 98 changes the direction of the tether 98 from a direction which is perpendicular or otherwise non-parallel to the longitudinal axis A of the container 14 to a direction which is parallel to and/or aligned with the longitudinal axis A of the container 14. The pulley member 98 may include a cylindrical drum or wheel that is rotatable relative to the main housing 29, or a cylindrical pin that is stationary relative to the main housing 29.

Prior to activation of the rotational power source 70, the tether 76 may be pulled taught between the stopper 34 and the winch drum 86 as a result of the stopper biasing member 74 exerting a biasing force on the stopper 34. At this moment in time, the tether 76 may prevent the stopper biasing member 74 from moving the stopper 34 through the reservoir 30, because the tether 76 is attached to the winch drum 86 which does not rotate to allow the tether 76 to unwind. Upon activation of the rotational power source 70, the winch drum 86 may rotate as a result of being mounted on the gear 84g. As the winch drum 86 rotates, the tether 76 may unwind and slack may be created in the tether 76. This slack may allow the stopper biasing member 74 to push the stopper 34 through the reservoir 30, thereby expelling the drug 32 from the container 14. Accordingly, the tether 76 may be configured to regulate the expansion of the stopper biasing member 74 by providing a braking functionality. In alternative embodiments, the tether 76 and the stopper biasing member 74 may be omitted, and instead a rack and pinion arrangement that receives rotational power via the gear 84g may push the stopper 34 through the reservoir 30.

Where appropriate, any of the above-described sub-assemblies, mechanisms, components, features, functionalities, methods of manufacture, methods of use, and other aspects of the drug delivery device 10 may be replaced with and/or combined with any of the sub-assemblies, mechanisms, components, features, functionalities, methods of manufacture, methods of use, and other aspects of the drug delivery devices described in some or all of the following documents, each of which is hereby incorporated by reference in its entirety for all purposes: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; International Patent Application No. PCT/US2017/017627 entitled "DRUG DELIVERY DEVICE, METHOD OF MANUFACTURE, AND METHOD OF USE"; and International Patent Application No. PCT/US2017/026524 entitled "DRUG DELIVERY DEVICE, METHOD OF MANUFACTURE, AND METHOD OF USE".

Methods of assembling the drug delivery device 10 will now be described. As a preliminary step, the empty container 14 and the seal member 40 may be connected together and sterilized. Next the container 14 and the seal member 40 may be aseptically transferred to a filling and capping environment. Here, the reservoir 30 of the container 14 may be filled with the drug 32, and then the proximal end 36 of the container 14 may be sealed closed with the stopper 34. This filling and capping environment may be operated as a sterile or aseptic assembly environment to ensure that microbes and other contaminants are not captured within the reservoir 30. Subsequently, the drug-filled container 14 may be packaged and shipped to a facility where the final assembly of the drug delivery device 10 is to occur.

Also, as a preliminary step, the gear module 72 may be assembled. This process may involve rotatably connecting each of the gears 84a-g to the mounting plate 82 and aligning the teeth of adjacent ones of the gears 84a-g such that the teeth meshingly engage each other when rotated. After the gears 84a-g have been rotatably connected to the mounting plate 82, the gears 84a-g may be visually inspected, either automatically with a sensor and/or camera and/or manually by a person, to ensure that gears 84a-g comply with one or more predetermined quality control measures. Such quality control measures include, but are not limited to, proper alignment of the teeth of adjacent ones of the gears 84a-g, proper pitch, proper tooth thickness at pitch circle, proper gear concentricity, proper gear grade, among others. Inspecting the gears at this stage may be easier as compared to inspecting them after installation in the main housing 29 of the drug delivery device 10 where they may be partially or entirely obstructed from view. After inspection of the gears 84a-g, the cover member 94 may be attached to the mounting plate 82 to cover the gears 84a-g and/or enclose them within the gear module 72. The assembly of the gear module 72 may occur at the final assembly facility, or at upstream assembly facility operated by an entity or company different from the operator of the final assembly facility.

At the final assembly facility, the pre-filled drug container 14 and the gear module 72 may be installed within the main housing 29 of the drug delivery device 10. Additionally, other components and mechanisms of the drug delivery device 10 may be installed within the main housing 29 at the final assembly facility such as the fluid pathway assembly 22, the insertion mechanism 12, the controller 26, components of the drive assembly 24 besides the gear module 72, and/or other components and mechanisms. Installing the gear module 72 in the main housing 29 may include connecting the mounting plate 82 to the interior surface 17 of the wall 15 of the main housing 29. This connection may be achieved by a fastener such as a bolt or screw and/or with an adhesive. In some embodiments, the assembly process may involve connecting the rotational power source 70 to the interior surface 17 of the wall 15 of the main housing 29 and subsequently connecting the gear module 72 to the interior surface 17 of the wall 15 of the main housing 29. In other embodiments, the order of these two steps may be reversed. Whichever the order of these two steps, installing the rotational power source 70 and the gear module 72 in the main housing 29 may involve aligning the teeth of the worm gear 80 with the teeth of the input gear 84a so that they meshingly engage each other when rotated. In alternative embodiments, the rotational power source 70 may be connected to the gear module 72, with the teeth of the worm gear 80 aligned with the teeth of the input gear 84a, prior to installation of the rotational power source 70 in the main housing 29. In such embodiments, the rotational power source 70 and the gear module 72 may be installed together in the main housing 29 as a single unit, rather than being installed separately.

Installing the gear module 72 within the main housing 29 may also involve operationally connecting the gear module 72 to the first end of the tether 76. In some embodiments, this may include wrapping a portion of the tether 76 multiple times around the exterior of the winch drum 86, and connecting the output gear 84g to the winch drum 86 such that the two components can rotate together about a common rotational axis. The assembly process may further involve operationally connecting the second end of the tether 76 to the stopper 34. The tether 76 may also be pulled taught partially around the pulley member 98 such that there is tension in the tether 76.

After all of the components have been mounted to the wall 15 of the main housing 29, any opening(s) in the wall 15 may be covered 15 to enclose the components within the main housing 29. In some embodiments, this step may involve creating an air-tight and/or fluid-tight seal to maintain a sterile or aseptic atmosphere within the main housing 29. Also, prior to or after enclosing the components within the main housing 29, the partially or fully assembled drug delivery device 10 may be subjected to a sterilization treatment such as radiation sterilization and/or gaseous sterilization such as ethylene oxide sterilization. At the completion of the final assembly stage, the drug delivery device 10 may be configured as a pre-loaded and pre-filled drug delivery device.

Drug Information

As mentioned above, the container may be filled with a drug. This drug may be any one or combination of the drugs listed below, with the caveat that the following list should neither be considered to be all inclusive nor limiting.

For example, the syringe may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the syringe may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgastrim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AblF; AblK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA ($\gamma$4), deposited at the ATCC under number PTA-5214, and a light chain encoded by a polynucleotide in plasmid 15H12/19D12 LCF ($\kappa$), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 14687;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No. 2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery device and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:
1. A drug delivery device comprising:
a main housing including an interior surface defining an enclosed space, and an exterior surface releasably attachable to a patient;
a container disposed in the enclosed space and including a reservoir containing a drug and a stopper;
a delivery member comprising a distal end configured to be inserted into a skin of the patient;
an insertion mechanism configured to, upon activation, move the delivery member from an initial position, wherein the distal end of the delivery member is disposed at least partially within the main housing, to a deployed position, wherein the distal end of the delivery member is disposed at least partially outside of the main housing for insertion into the skin of the patient; and
a drive assembly disposed in the enclosed space and configured to activate the insertion mechanism and expel the drug from the reservoir, the drive assembly including a rotational power source and a gear module, the gear module including a mounting plate and a plurality of gears rotatably connected to the mounting plate, wherein the mounting plate is separate from the main housing.

2. The drug delivery device of claim 1, the mounting plate including a bottom surface facing the interior surface of the housing, and a top surface where the plurality of gears is disposed.

3. The drug delivery device of claim 1, wherein a first rotational axis of a first gear of the plurality of gears is offset from and parallel to a second rotational axis of a second gear of the plurality of gears, and wherein teeth of the first gear meshingly engage teeth of the second gear during operation of the rotational power source.

4. The drug delivery device of claim 1, the drive assembly comprising:
- a stopper biasing member initially retained in an energized state and configured to expand to move the stopper through the reservoir when released from the energized state; and
- a tether connected between the stopper and the gear module and configured to regulate expansion of the stopper biasing member.

5. The drug delivery device of claim 4, the rotational power source being operationally connected to the tether via the plurality of gears, and wherein rotation of the plurality of gears creates slack in the tether which allows the stopper biasing member to expand.

6. The drug delivery device of claim 4, comprising a pulley member in contact with a portion of the tether extending between the gear module and the stopper.

7. The drug delivery device of claim 1, comprising a worm gear mounted on an output shaft of the rotational power source and having teeth that meshingly engage with teeth of at least one gear of the plurality of gears during operation of the rotational power source.

8. The drug delivery device of claim 7, wherein the rotational power source is directly connected to the mounting plate and the output shaft is configured to rotate relative to the mounting plate.

9. The drug delivery device of claim 1, wherein the delivery member comprises a subcutaneous delivery member.

10. The drug delivery device of claim 1, wherein the insertion mechanism comprises an insertion biasing member initially retained in an energized state and configured to move the delivery member from the initial position to the deployed position when released from the energized state.

11. The drug delivery device of claim 1, the plurality of gears including three or less gear pairs arranged in series.

12. The drug delivery device of claim 1, wherein the drive assembly is configured to expel the drug from the reservoir by moving the stopper through the reservoir.

* * * * *